US012806354B2

(12) United States Patent
Beda et al.

(10) Patent No.: US 12,806,354 B2
(45) Date of Patent: Nov. 24, 2026

(54) METHOD AND VENTILATION APPARATUS FOR DETERMINING A RESPIRATORY-GAS CONTENT IN A RESPIRATORY TRACT DURING ARTIFICIAL VENTILATION

(71) Applicant: Hamilton Medical AG, Bonaduz (CH)

(72) Inventors: Alessandro Beda, Rhäzüns (CH); Federico Alexander Wadehn, Bonaduz (CH); Johannes Meyer, Chur (CH); Dominik Novotni, Chur (CH)

(73) Assignee: Hamilton Medical AG, Bonaduz (CH)

( * ) Notice: Subject to any disclaimer, the term of this patent is extended or adjusted under 35 U.S.C. 154(b) by 718 days.

(21) Appl. No.: 18/273,665

(22) PCT Filed: Feb. 7, 2022

(86) PCT No.: PCT/EP2022/052837

§ 371 (c)(1),
(2) Date: Jul. 21, 2023

(87) PCT Pub. No.: WO2022/167638

PCT Pub. Date: Aug. 11, 2022

(65) Prior Publication Data

US 2024/0299688 A1 Sep. 12, 2024

(30) Foreign Application Priority Data

Feb. 8, 2021 (DE) ..................... 10 2021 102 886.8

(51) Int. Cl.
*A61M 16/00* (2006.01)

(52) U.S. Cl.
CPC ..................... *A61M 16/024* (2017.08); *A61M 2016/0036* (2013.01); *A61M 2205/50* (2013.01)

(58) Field of Classification Search
CPC ................ A61M 16/024; A61M 16/04; A61M 16/0816; A61M 16/0833; A61M 16/0858;
(Continued)

(56) References Cited

U.S. PATENT DOCUMENTS

| | | | | |
|---|---|---|---|---|
| 5,915,381 | A * | 6/1999 | Nord .................. | A61M 16/024 128/204.26 |
| 8,757,152 | B2 | 6/2014 | Milne et al. | |
| 9,636,472 | B2 | 5/2017 | Rueller et al. | |
| 10,137,266 | B2 | 11/2018 | Shelly et al. | |

(Continued)

FOREIGN PATENT DOCUMENTS

| | | | |
|---|---|---|---|
| CN | 101756703 | A | 6/2010 |
| CN | 208864968 | U | 5/2019 |

(Continued)

OTHER PUBLICATIONS

German Search Report for corresponding DE 10 2021 102 886.8 mailed Nov. 22, 2021, 6 pgs.

(Continued)

*Primary Examiner* — Tu A Vo
*Assistant Examiner* — Kelsey E Baller
(74) *Attorney, Agent, or Firm* — Rankin, Hill & Clark LLP

(57) ABSTRACT

A method for determining a respiratory-gas content in a respiratory tract including quantitative detection of inspiratory and expiratory respiratory-gas flows by at least one respiratory-gas flow sensor and summation of detected inspiratory and expiratory flow values to form the respiratory-gas content in the respiratory tract; wherein a respiratory tract content starting value, at which the determination of the respiratory-gas content in the respiratory tract for the follow-up breath starts, depending on a difference in respiratory-gas amount between an inspiratory respiratory-gas amount supplied to the patient during an earlier number of breaths and an expiratory respiratory-gas amount output by the patient during the earlier number of breaths, is set to a reset starting value, which is closer to zero than to a difference value that quantitatively provides the respiratory-gas amount difference, or is set to a continuity starting value, which is closer to the difference value than to zero.

18 Claims, 3 Drawing Sheets

(58) Field of Classification Search
CPC .......... A61M 16/0875; A61M 16/0883; A61M 16/109; A61M 16/16; A61M 2016/0036; A61M 2016/0027; A61M 2205/50; A61M 2205/502; A61M 2209/045; A61M 2209/084
See application file for complete search history.

(56) References Cited

U.S. PATENT DOCUMENTS

| | | | | |
|---|---|---|---|---|
| 10,874,811 | B2 | 12/2020 | Gholami et al. | |
| 11,154,217 | B2 | 10/2021 | Stenqvist | |
| 11,464,703 | B2 | 10/2022 | Johnson et al. | |
| 2002/0023644 | A1 | 2/2002 | Berthon-Jones | |
| 2006/0086358 | A1 | 4/2006 | Kushnir et al. | |
| 2006/0130835 | A1 * | 6/2006 | Truschel ............. | A61M 16/204<br>128/204.23 |
| 2009/0159082 | A1 | 6/2009 | Eger | |
| 2012/0137249 | A1 | 5/2012 | Milne et al. | |
| 2015/0040905 | A1 * | 2/2015 | Kulstad ................. | A61M 16/10<br>128/204.23 |
| 2020/0282163 | A1 | 9/2020 | Schranz et al. | |

FOREIGN PATENT DOCUMENTS

| | | | | |
|---|---|---|---|---|
| DE | 102017217859 A1 | 8/2018 | | |
| WO | WO-2019094736 A1 * | 5/2019 | ............. | G16H 50/20 |

OTHER PUBLICATIONS

International Search Report for corresponding PCT/EP2022/052837 mailed May 19, 2022, 13 pgs.
Chinese Office Action for corresponding CN 202280011388.8 mailed Jul. 4, 2025, 6 pgs.
Espacenet Bibliographic data: CN 101756703 (A), Published Jun. 30, 2010, 1 pg.
Espacenet Bibliographic data: DE 102017217859 (A1), Published Aug. 16, 2018, 2 pgs.
Chinese Search Report for corresponding CN 202280011388.8 mailed Oct. 17, 2025, 4 pgs.
Espacenet Bibliographic data: CN 208864968(U), Published May 17, 2019, 1 pg.
International Preliminary Report On Patentability for corresponding PCT/EP2022/052837 mailed Aug. 3, 2023, 7 pgs.

* cited by examiner

METHOD AND VENTILATION APPARATUS FOR DETERMINING A RESPIRATORY-GAS CONTENT IN A RESPIRATORY TRACT DURING ARTIFICIAL VENTILATION

This application claims priority in PCT application PCT/EP2022/052837 filed on Feb. 7, 2022, which claims priority in German Patent Application DE 10 2021 102 886.8 filed on Feb. 8, 2021, which are incorporated by reference herein.

The present invention concerns a method for determining respiratory gas content in a respiratory tract, which is present in the respiratory tract of an at least partially artificially ventilated patient after several breaths performed under the participation of a ventilation apparatus, where the several breaths exhibit at least one earlier breath set and at least one subsequent breath following the earlier breath set. The earlier breath set exhibits one earlier breath or a plurality of successive earlier breaths. The method comprises quantitative acquisition of inspiratory and expiratory respiratory gas flows through at least one respiratory gas flow sensor and it comprises summation of acquired inspiratory and expiratory flow values to the respiratory tract content of respiratory gas.

The invention further concerns a ventilation apparatus for at least partial artificial ventilation of a patient, configured to perform the method being described here.

BACKGROUND OF THE INVENTION

In principle, respiratory gas volumes in ventilation apparatuses are ascertained through integration, due to the use of digital data processing normally numerical integration, of the acquired respiratory gas flows over the time of interest. Thus in ventilation apparatuses, the administered inspiratory respiratory gas quantity is ascertained through integration of the acquired inspiratory respiratory gas flows, i.e. the respiratory gas flows streaming towards the patient, from the beginning of the inspiration process until its end. Likewise, the expiratory respiratory gas quantity exhaled by the patient can be ascertained through integration of the acquired expiratory respiratory gas flows over the duration of the expiration process, i.e. from the beginning of the expiration process until its end.

Knowledge of for example inspiratory respiratory gas volumes can be important for controlling a ventilation apparatus, in order to ascertain whether the tidal volume determined by the treating personnel (i.e. in volume-related ventilation control, the respiratory gas quantity to be administered per breath) has been administered to a patient. If this is the case, then for example a ventilation apparatus operating in a volume-controlled ventilation mode switches control over from inspiration to expiration.

Often, respiratory gas flows are acquired and integrated continuously in order to know the respiratory gas present or remaining at each point in time in the respiratory tract of the patient. Here, inspiratory and expiratory respiratory gas flows, due to their opposite direction, once towards the patient and once away from the patient, are distinguished through different mathematical signs. Thus when integrating the respiratory gas flows, there is first accumulated quantitatively during an inspiration process an inspiratory respiratory gas quantity in the patient and subsequently decreased again quantitively during a following expiration process.

Ideally, during the expiration phase the same quantity of respiratory gas flows away from the patient which previously in an inspiration phase flowed towards the patient. However, it can happen that flow sensors in ventilation apparatuses acquire the respiratory gas flows in opposite flow directions at a different accuracy, be it due to deficient calibration or be it due to fabrication inaccuracies which can manifest themselves as directionally asymmetrical acquisition accuracy. Deficient calibration can, for example, arise through contamination of a flow sensor with humidity from the respiratory gas which precipitates in the region of the flow sensor. Through increasing or varying humidity contamination, the flow sensor deviates increasingly or to a varying extent from its calibration. The humidity can precipitate at a different intensity upstream and downstream of the flow sensor, in particular a differential pressure flow sensor, thus causing asymmetrical acquisition behavior with respect to the flow direction of the respiratory gas.

The consequence is then drift of the sensor signal representing the respiratory volume, observable over several breaths. Due to this drift, the sensor signal deviates increasingly over time quantitatively from a theoretical error-free sensor signal.

In order to prevent such drift, some state-of-the-art ventilation apparatuses are configured to determine the respiratory gas content of the respiratory tract of the patient (respiratory tract content of respiratory gas) separately for each breath, independently from the acquisition result of the respiratory tract content for the immediately preceding breath. This corresponds, in continuous acquisition of the respiratory tract content of respiratory gas, to resetting the acquired respiratory tract content at the end of an earlier breath to zero, such that the acquisition of the respiratory tract content for the subsequent breath begins at zero.

Indeed, the described drift can thereby be prevented, but there exists the risk that such regular resetting of the summed acquisition of the inspiratory and expiratory respiratory gas volumes conceals other events relevant for evaluating a ventilation process, such as for example what is referred to as 'breath stacking', for instance triggered through 'double triggering' or through a short expiration, which can be understood in German as 'Atemstapelung' (='breath stacking'). During this event, no expiration or only an incomplete one takes place between two triggered inspiration processes such that in the subsequent breath after the incomplete expiration, the tidal volume specified in the ventilation apparatus is again administered on top of the significant respiratory gas residual quantity remaining in the respiratory tract of the patient as respiratory tract content. Since the respiratory tract content remaining in the respiratory tract of the patient at the end of the incomplete expiration process of the earlier breath is not recognized, because of the resetting to zero in the acquisition of the respiratory gas volumes, with the administration of the tidal volume in the subsequent breath there is created in the respiratory tract of the patient an undesirably high respiratory gas pressure and an undesirably high respiratory gas volume, which at the least is unpleasant for the patient but means an undesirable medical risk.

From U.S. Pat. No. 8,757,152 B1 there are known various methods to infer, on the basis of ventilation parameters of a current ventilation process, the occurrence of double triggering of an inspiration process. These methods, however, have no impact on the determination of the respiratory tract content of respiratory gas in a subsequent breath following an earlier breath.

SUMMARY OF THE INVENTION

It is, therefore, the task of the present invention further to develop the method mentioned in the beginning for determining a respiratory tract content of respiratory gas and a ventilation apparatus configured for implementing the method in such a way that drift of a sensor signal representing the respiratory tract content of respiratory gas of a patient can be prevented sufficiently reliably, without thereby disregarding medically relevant breath stacking.

The present invention solves this task in the method mentioned in the beginning by having a respiratory tract content starting value with which the determination of the respiratory tract content of respiratory gas for the subsequent breath begins, depending on a respiratory gas quantity difference between an inspiratory respiratory gas quantity supplied to the patient during the earlier breath set and an expiratory respiratory gas quantity exhaled by the patient during the earlier breath set, set to a reset starting value lying nearer to zero than to a difference value indicating quantitatively the respiratory gas quantity difference or to a continuity starting value lying nearer to the difference value than to zero. Hence, for example when the respiratory gas quantity difference is quantitatively small, for instance smaller than a difference threshold value, the reset starting value can be set as respiratory tract content starting value. This should be the normal case of an artificial ventilation, such that the described drift can be prevented by using the reset starting value. Furthermore, when the respiratory gas quantity difference is quantitatively large, for instance larger than the difference threshold value, the continuity starting value can be set as the respiratory tract content starting value. This makes it possible to notice exceptional ventilation events which are manifested in the respiratory gas quantity inhaled and exhaled by the patient, and nevertheless to avoid undesirable signal drift.

Thus, small quantitative deviations of the inspiratory and the expiratory respiratory gas quantity from one another can be levelled out and/or masked out respectively, whereas deviations which are quantitatively sufficiently large to be taken into account are transferred as a starting value into the determination of the respiratory tract content of respiratory gas for the subsequent breath. Consequently, the determination of the respiratory tract content of respiratory gas for the subsequent breath takes into account that the respiratory tract of the patient at the beginning of the subsequent breath is already partly filled with respiratory gas.

The term 'respiratory tract' denotes the upper and the lower airways of a patient. The body organ commonly referred to as 'lung' belongs to the lower airways.

Preferably, the summation of the inspiratory and the expiratory respiratory gas flows over the plurality of breaths is a balance-sheet summation, in which opposite respiratory gas flows are factored in with different mathematical signs. For example, all respiratory gas flows supplied to the patient can be positive, whereas all respiratory gas flows streaming away from the patient are negative. The result of the continual summation of respiratory gas flows with different signs is that equally directed respiratory gas flows of one and the same breath segment, for instance of an inspiration process, are summed to a quantitatively increasing inspiratory respiratory gas volume, and that this respiratory gas volume in a subsequent expiration process as a further breath segment with respiratory gas flows which within the expiration process are equal among themselves but are directed oppositely to the preceding inspiration process is quantitatively decreased again through the continued summed respiratory gas flows with opposite signs. At each point in time during a breath, the respiratory gas volume thus determined indicates sufficiently accurately the current respiratory tract content of respiratory gas of the patient. If the determination of the respiratory tract content of respiratory gas starts at the beginning of the first breath supported by the ventilation apparatus with an initial respiratory tract content of respiratory gas, then the respiratory tract content of respiratory gas ascertained over the plurality of respiratory gas breaths carried out thus far indicates the change against the initial respiratory tract content of respiratory gas. Since determining a respiratory tract content of respiratory gas present in a respiratory tract of a patient, outside of artificial ventilation, involves considerable cost in resources, normally the aforementioned initial respiratory tract content of respiratory gas is zero. The respiratory tract content of respiratory gas determined with the method being proposed here is, therefore, preferably a respiratory tract content of respiratory gas additionally to the normally unknown initial respiratory tract content of respiratory gas. The respiratory tract content of respiratory gas therefore indicates that part of a respiratory gas quantity moved in total by the ventilation apparatus during a ventilation treatment which currently remains in the respiratory tract of the patient.

The difference value indicates quantitatively the respiratory gas quantity difference between the total inspiratory respiratory gas quantity supplied in the earlier breath set and the total expiratory respiratory gas quantity flowing away from the patient in the same earlier breath set, which corresponds, neglecting any leakage losses in the valves and in the lines conducting respiratory gas of the ventilation apparatus as well as where applicable also in the region of the respiratory tract itself, to the respiratory tract content of respiratory gas present in the respiratory tract of the patient at the end of the earlier breath set.

To clarify, a breath according to the present application comprises at least one inspiration process, normally also an expiration process. The expiration process can, as described above, be incomplete due to breath stacking and/or double triggering as the case may be, where the complete absence of an expiration process also comes under incompleteness of an expiration process.

In principle, it is conceivable to choose the reset starting value in a predetermined range of values that lies nearer to zero than to the difference value. The same applies mutatis mutandis to the continuity starting value, which can be chosen in a predetermined range of values that lies nearer to the difference value than to zero. In order to avoid drift completely and reliably, preferably the reset starting value equals zero. Additionally or alternatively, preferably the continuity starting value is the difference value, in order to make sure that the determination of the respiratory tract content starting value for the subsequent breath begins with the respiratory tract content respiratory gas quantity at the end of the earlier breath set immediately preceding the subsequent breath as starting value. An integration of respiratory gas flows continuing beyond a breath limit, such that the determination of the respiratory tract content starting value for the subsequent breath begins with the respiratory tract content respiratory gas quantity at the end of the earlier breath set immediately preceding the subsequent breath as starting value, is a setting of the respiratory tract content starting value at the difference value within the meaning of the present application.

Preferably, the respiratory tract content starting value is determined repeatedly during a uniform, continuous ventilation treatment of a patient, in order to mask out a drift error during the longest possible time period of the artificial ventilation, without however also masking out breath stacking.

In principle, it is further conceivable to correct each drift, if any, only after a predetermined number of breaths, such that the earlier breath set can comprise a plurality of immediately successive earlier breaths. The earlier breath set is followed by a subsequent breath, for which the respiratory tract content starting value should be determined. If, however, the earlier breath set contains too many breaths, in some circumstances a drift error added up over these many breaths can be distinguished from breath stacking with otherwise drift-free acquisition of the respiratory tract content of respiratory gas only with difficulty and thereby with an undesirably high error rate.

In order to make sure that a drift error for the determination of the respiratory tract content starting value of the subsequent breath is sufficiently clearly distinguishable from the effect of breath stacking, according to a preferred further development of the present invention it is the case for a plurality of successive breaths that the earlier breath set contains exactly one earlier breath. This makes possible the further advantageous further development that for every earlier breath out of a plurality of earlier breaths, a respiratory tract content starting value is determined for the respective subsequent breath as a function of the respiratory gas quantity difference. In this case, breaths which in a determination of a respiratory tract content starting value are subsequent breaths, are each an earlier breath in a following determination of the respiratory tract content starting value.

In a simple but robust embodiment of the method, the difference value itself can be used as a criterion, in order to decide whether the reset starting value or the continuity starting value is set as the respiratory tract content starting value. Greater freedom in the forming of the decision for a respiratory tract content starting value, and thereby as a result higher accuracy in the determination of the respiratory tract content of respiratory gas, can be obtained by the method additionally comprising the determination of a decision value, where the decision value represents the respiratory gas quantity difference.

In this process it can suffice if the decision value represents the respiratory gas quantity difference qualitatively or indirectly. For example, the decision value can assess the respiratory gas quantity difference on the basis of a difference between the temporal duration of the at least one inspiration process and the temporal duration of the at least one expiration process of the earlier breath set and from the difference between the aforementioned temporal durations infer a difference between the associated inspiratory and expiratory respiratory gas quantities. The decision value can be a predetermined function of the temporal duration of the at least one inspiration process and of the temporal duration of the at least one expiration process of the earlier breath set. The decision value can for example be proportional to a ratio of the temporal duration of the at least one inspiration process and the temporal duration of the at least one expiration process of the earlier breath set.

An especially accurate decision for the one or the other respiratory tract content starting value can be made when the decision value represents the difference value. The decision value can be a predetermined function of the difference value. Advantageous embodiments of the decision value are discussed further below. In the determination of the respiratory tract content starting value, the reset starting value or the continuity starting value can then be determined as the respiratory tract content starting value as a function of the decision value.

When, as described above, for a plurality of successive breaths it is the case that the earlier breath set contains exactly earlier breath, consequently for each out of a plurality of earlier breaths a decision value can be ascertained and depending on the respective decision value a respiratory tract content starting value determined for each subsequent breath following an earlier breath out of the plurality of earlier breaths.

Using a decision value which differs quantitatively from the difference value but represents the difference value makes it possible, for example, in a way which is advantageous for the informative value of the decision value, to set the difference value in relationship to the total respiratory gas quantity moved during the earlier breath set, because a given absolute parameter of a ventilation treatment, such as for instance part-breath duration in seconds or difference value in volume, mass, or weight should be evaluated medically differently depending on whether it has occurred in a ventilated small child or in a ventilated adult.

Preferably the decision value sets the difference value in relationship to the inspiratory respiratory gas quantity supplied to the patient during the earlier breath set. The decision value can therefore be proportional to a ratio of the difference value and an inspiratory respiratory gas quantity supplied to the patient under participation of the ventilation apparatus during the earlier breath set. The proportionality factor can be chosen in accordance with the characteristic of the respective ventilation apparatus being used, for instance taking into account a leakage loss occurring at each breath. It suffices, however, to choose for the proportionality factor the value 1, such that the decision value equals the aforementioned ratio. As a ratio there also counts its inverse, which has the same information content and therefore the same informative value. As already indicated above, the decision value can be the difference value itself, although for the aforementioned reasons this is not preferred.

The determination of the respiratory tract content starting value as a function of the decision value can advantageously comprise a comparison of the decision value with a predetermined decision threshold value, where the determination of the respiratory tract content starting value depends on a result of the comparison. The decision threshold value can be so chosen, in accordance with an experimental series on the ventilation apparatus being used, that the error rate of breath stackings identified undesirably as false-positive but which actually did not occur and/or of actual breath stackings identified undesirably as false-negative is as low as possible.

In the preferred repeated determination of a respiratory tract content starting value during artificial ventilation, artefacts can occur which progressively over time paint an increasingly unrealistic picture of the respiratory gas quantity actually moved during the artificial ventilation.

For example, the applicant knows from medical observations that breath stackings cannot occur arbitrarily often one after the other, since the physically limited respiratory tract volume of a patient makes it impossible to administer to an incompletely exhaling patient arbitrarily frequently one after the other the tidal volume set at the ventilation apparatus. Therefore, in the method proposed here it can be provided in multiple determination of a respiratory tract content starting value for different breaths to set the reset starting value independently from the respiratory gas quantity difference, in particular independently from the decision value, as the respiratory tract content starting value when previously in a predetermined first number of successive determinations of the respiratory tract content starting value each time the continuity starting value was set as the respiratory tract content starting value. In investigations thus far, 4 has proved to be a suitable predetermined first number, although the first number can also be 3 or 5 or even 6.

Under the same aspect of a physiologically impossible too frequent administration of the tidal volume without adequate intermediate expiration, the reset starting value can be set as the respiratory tract content starting value independently from the respiratory gas quantity difference, in particular independently from the decision value, when previously within a predetermined second number of determinations of the respiratory tract content starting value the number of determinations which had as a result the continuity starting value reaches or exceeds a predetermined fraction threshold value, where the fraction threshold value is smaller than the second number. Likewise, the second number is preferably larger than the first number. The fraction threshold value can be a percentage threshold value or an absolute threshold value. For example, the fraction threshold value can be 50% or the fraction threshold value can be 5 determinations with a second number of 10 determinations. With a fraction threshold value defined as a percentage, the second number of determinations can be changed as a reference variable in a data processing program which effects the implementation of the proposed method at a lower cost in resources than with an absolutely defined fraction threshold value.

Likewise, it can alternatively or preferably additionally be provided that the reset starting value is determined as the respiratory tract content starting value independently from the respiratory gas quantity difference, in particular independently from the decision value, when within a predetermined number of previously performed breaths it is the case that a frequency at which a ratio of a first respiratory tract content difference and a second respiratory tract content difference which differs from the first reaches or exceeds a predetermined ratio threshold value, reaches or exceeds a frequency threshold value. The first respiratory tract content difference is preferably a difference between the respiratory tract content of respiratory gas at the end of a particular breath and the respiratory tract content of respiratory gas at the end of an earlier breath set preceding the particular breath. The second respiratory tract content difference is preferably a difference between a respiratory tract content of respiratory gas at the end of an inspiration phase of the particular breath and the respiratory tract content of respiratory gas at the end of the earlier breath set preceding the particular breath. Expressed as a formula, this means for a preferred embodiment example:

$$\frac{V_{endexp,i} - V_{endexp,i-1}}{V_{endinsp,i} - V_{endexp,i-1}} \geq QS \quad \text{Eq. 1}$$

The incremental or counting index i refers to the later considered breath, i.e. in the above terminology the particular breath within the predetermined number of previously performed breaths. The particular breath is freely selectable, but should not be the first breath of the ventilation process since a breath has to precede it. Preferably, the particular breath is the breath directly preceding the subsequent breath.

The incremental or counting index i−1 thus refers to the earlier breath set directly preceding the particular breath, in particular to the directly preceding earlier breath. In Equation 1, $V_{endexp,i}$ denotes the respiratory tract content of respiratory gas at the end of a particular breath, i.e. at the end of the expiration phase of the particular breath; $V_{endexp,i-1}$ denotes the respiratory tract content of respiratory gas at the end of the earlier breath set preceding the particular breath, in particular of an earlier breath, i.e. again at the end of an expiration phase; $V_{endinsp,i}$ denotes the respiratory tract content of respiratory gas at the end of an inspiration phase of the subsequent breath, and QS is the ratio threshold value. The ratio threshold value can be ascertained on the basis of experimental investigations. It lies preferably between 0.1 and 0.3, preferably between 0.15 and 0.25, and especially preferably equals 0.2.

The frequency threshold value as a percentage threshold value can equal approximately 40% to 80%. The frequency threshold value preferably lies in a range between 40% and 60%, and especially preferably equals 50%.

The predetermined frequency can equal between 5 and 20 breaths, preferably between 8 and 15 breaths, and especially preferably equals 10 breaths.

A further possibility of an erroneous assessment of the respiratory tract content of respiratory gas can arise from a change in the positive end-expiratory pressure (PEEP=Positive End-Expiratory Pressure) taking place during the artificial ventilation. A change in the PEEP means, due to the known relationships between pressure and volume in gases, also a change in the end-expiratory respiratory tract content of respiratory gas. For advantageous prevention of an erroneous assessment of the respiratory tract content of respiratory gas caused by a change in the PEEP, under the proposed method it can be provided that the reset starting value is determined as the respiratory tract content starting value independently from the respiratory gas quantity difference, in particular independently from the decision value, when within a predetermined time interval before the current determination of the respiratory tract content starting value a quantitative change in the PEEP was acquired. The predetermined time interval can be defined relatively, based on a reference time interval. The predetermined time interval and/or the reference time interval can be defined absolutely as a time interval in seconds, minutes, and the like. The predetermined time interval and/or the reference time interval can, however, just as well be defined functionally, for instance through the duration of a predetermined number of earlier breaths or breath segments. A breath segment can for example be the inspiration phase or the expiration phase of the breath.

Furthermore, during artificial ventilation, in particular after breath stacking but also otherwise, there occur occasionally above-average deep expiration processes in which the patient exhales more expiratory respiratory gas than the patient inhaled during the preceding inspiration phase. After such a deep expiration with an above-average expiratory respiratory gas volume, there is the highest probability that the respiratory tract of the patient is not part-filled with respiratory gas to a medically critical extent. Therefore, the reset starting value can be determined as the respiratory tract content starting value independently from the respiratory gas quantity difference, in particular independently from the decision value, when for at least one of the two earlier breath sets directly preceding the current subsequent breath for which the respiratory tract content starting value is being determined, in particular for at least one of the two directly preceding earlier breaths, it is ascertained that an expiratory respiratory gas volume of the earlier breath set ascertained from the acquired expiratory respiratory gas flows is quantitatively greater than an inspiratory respiratory gas volume of the same earlier breath set ascertained from the inspiratory respiratory gas flows. This means, in a preferred embodiment, for one thing that directly after an aforementioned deep expiration the determination of the respiratory tract content can begin with the reset starting value, since in this case no breath stacking threatens. This means, in a preferred embodiment, for another thing that the determination of the respiratory tract content directly after an incomplete expiration can begin with the reset starting value even when a deep expiration has taken place directly before the incomplete expiration. In this second case, breath stacking indeed takes place, but in a previously over-expired respiratory tract, such that even after the incomplete expiration no excessive stressing of the respiratory tract through the breath stacking is to be feared.

To facilitate monitoring of the ventilation process, the respiratory gas content in a respiratory tract can be output graphically as a function of time in an output device.

The aforementioned objective technical task is also solved through a ventilation apparatus for at least partial artificial ventilation of a patient, comprising:

- A respiratory gas source arrangement which provides an inspiratory respiratory gas for artificial ventilation of the patient,
- A flow modification device which is configured to create and quantitatively to modify an inspiratory respiratory gas flow,
- A respiratory gas line arrangement with a proximal longitudinal end which during operation lies nearer to the patient and with a distal longitudinal end which during operation lies further away from the patient, in order to convey the inspiratory respiratory gas flow from the respiratory gas source arrangement up to the patient,
- A flow sensor arrangement which is configured quantitatively to acquire the inspiratory respiratory gas flow and likewise an expiratory respiratory gas flow,
- A control device with a data store, where the control device is linked for signal transmission with the data store and with the flow sensor arrangement and which is configured to control the operational performance of the flow modification device for modifying the inspiratory respiratory gas flow, where the control device is configured to implement the method described above and advantageously further developed. The control device can exhibit a processor with integrated circuits and a data store with a program stored on it which can be retrieved and processed by the processor, where the execution of the program by the processor leads to the implementation of the method described above.

The respiratory gas source arrangement of the ventilation apparatus can as a respiratory gas source exhibit an aspiration port, through which ambient air or gas can be aspirated from a predetermined gas supply. The respiratory gas source arrangement can additionally or alternatively exhibit a gas supply as a respiratory gas source, for example as a storage container or as a connector formation for connecting a supply line which connects the ventilation apparatus with a locally installed gas supply, as is often the case in hospitals. In order to provide the option of mixing different gases into a respiratory gas, the respiratory gas source arrangement can exhibit a plurality of individual respiratory gas sources, such as the ones mentioned above. The different gases to be mixed can, due to their individual preparation and expansion, exhibit different temperatures and/or different humidity. In order to make sure that the inspiratory respiratory gas actually reaches the patient with the once adjusted humidity, especially preferably no more respiratory gas component is added in the inspiration direction downstream from a preferably present humidification device to the respiratory gas flow exiting from the humidification device.

The flow sensor arrangement can exhibit one or several flow sensors, for instance one each for the inspiratory and for the expiratory respiratory gas flow. Preferably the flow sensor arrangement comprises only one flow sensor to acquire both the inspiratory and the expiratory respiratory gas flow. It is preferably arranged proximally between the respiratory gas line arrangement and a patient interface, but can also be accommodated distally in a housing of the ventilation apparatus, in which for example the flow modification device is also accommodated. To achieve higher process reliability, the ventilation apparatus can also exhibit several flow sensors each of which acquires both the inspiratory and the expiratory respiratory gas flow, for instance one distal flow sensor in a housing of the ventilation apparatus and one proximal flow sensor near the patient.

The ventilation apparatus preferably exhibits a pressure sensor arrangement, which likewise can exhibit one or several pressure sensors, in order to measure the pressure of the inspiratory and/or the expiratory respiratory gas.

The flow sensor arrangement preferably comprises a differential pressure flow sensor, such that with the differential pressure flow sensor at the point of acquisition of the respiratory gas flow, acquisition of the respective prevailing respiratory gas pressure is also possible. Especially preferably, the flow sensor arrangement is a proximal, patient-near flow sensor arrangement. For example, the proximal flow sensor arrangement with which the respiratory gas flows for determining the respiratory tract content starting values are acquired is no further away than 80 cm, preferably no further away than 50 cm, from the mouth of the patient. A proximal flow sensor arrangement exhibits better synchrony than a distal flow sensor arrangement further away from the patient, thus allowing more accurate acquisition of triggering of an inspiration process caused by the patient, i.e. an inspiration effort of the patient.

The ventilation apparatus, in particular the control device, preferably also comprises a timing device in order to be able to ascertain durations of processes and part-processes during a ventilation treatment.

In order to realize the graphic output of the determined respiratory tract content of respiratory gas as a function of time, the ventilation apparatus preferably exhibits a graphic output device, for instance a monitor or a touchscreen. The control device is then preferably configured to output the determined respiratory tract content of respiratory gas as a function of time graphically on the output device.

In order to provide a therapist accompanying the artificial ventilation of a patient with the simple possibility of recognizing a potentially critical breath stacking quickly and reliably, the graphic output of the respiratory gas content in a respiratory tract as a function of time can comprise at the output device the measure of changing the graphic output of the respiratory tract content as a function of time when the continuity starting value is set as the respiratory tract content starting value.

The changing of the graphic output can be a change in the graph of the respiratory tract content as a function of time, for instance a change in the line color and/or in the line thickness, for instance between thinner and thicker line weight, and/or of the type of line, for instance between dotted and/or dashed and/or continuous line.

Additionally or alternatively, the change in the graphic output can be a change in at least one section of the background on which the graph of the respiratory tract content as a function of time is output. For example, the color and/or the texture, for instance between hatched and uniform, of the background can be changed. Here, either the whole background or only one between the graph and a reference line, for instance the zero line of the respiratory tract content, can be changed.

In principle, the change in the graphic output can be a change in the whole graphic output, also of parts which depict the temporal course of the respiratory tract content in the past. This applies in particular, but not only, to changing the background.

Facilitated recognition not only that breath stacking has taken place, but also when this has happened, can be made possible for the accompanying therapist in an advantageous manner by having the change in the graphic output carried out only from the point in time of choosing the continuity starting value as the respiratory tract content starting value and already output graphic contents, which continue to be depicted, remaining unchanged.

The ventilation apparatus is accordingly configured to carry out this unchanged graphic output.

For input and completely generally for output of data, the ventilation apparatus preferably comprises an input/output device controllable by the control device, to which the aforementioned graphic output device can also belong. The input/output device can comprise a plurality of keys, rotary switches, a touchscreen, a speaker, lamps, and the like. Likewise, the ventilation apparatus can exhibit data interfaces and/or data transmission lines in order to receive data from other devices and/or to transmit data to these. Data interfaces can be sockets, radio antennas, plugs, and the like.

In principle, the ventilation apparatus is preferably configured to ventilate a patient in accordance with different ventilation modes out of which the treating physician can choose when adjusting the ventilation apparatus. For example, the ventilation apparatus can artificially ventilate a patient under volume-related control or pressure-related control. Since breath stacking and/or double triggering as the case may be occur first and foremost when performing supporting and/or support ventilation modes respectively, in which a patient through an inspiration effort can trigger artificial inspiration which is then supported by the ventilation apparatus, the ventilation apparatus is preferably configured to perform artificial ventilation in a support ventilation mode in which the control device acquires an inspiration of the ventilated patient, and on acquiring the inspiration effort actuates the flow modification device to administer to the patient an inspiratory respiratory gas quantity via the respiratory gas line arrangement. An inspiration effort can for example be acquired by monitoring a respiratory gas flow and/or a respiratory gas pressure in the respiratory gas line arrangement for sudden typical changes.

In order to mitigate the effects of undesirable breath stacking and/or double triggering respectively, the control device is preferably configured to recognize an incomplete expiration on the basis of the respiratory tract content starting value determined in accordance with the method and/or on the basis of the determined respiratory gas content in a respiratory tract. When the continuity starting value is set as the respiratory tract content starting value, an incomplete expiration can be recognized simply and reliably by one or several threshold values for the respiratory tract content of respiratory gas being exceeded during a following inspiration. The control device is preferably configured, when the control device has recognized an incomplete expiration, to change the ventilation mode, in particular between a volume-relatedly controlled ventilation mode and a pressure-relatedly controlled ventilation mode. Of special interest here is the change from a volume-relatedly controlled ventilation mode, which threatens to 'overfill' the incompletely exhaled respiratory tract, to a pressure-relatedly controlled ventilation mode, which for example controls for a respiratory gas pressure value to be reached during an inspiration and not for the supply of a predetermined tidal volume.

The previously designated respiratory gas quantity can be a mass, a weight, or a volume of respiratory gas. Preferably, the respiratory gas quantity is a respiratory gas volume as is preferred and usual in medical ventilation technology.

These and other objects, aspects, features and advantages of the invention will become apparent to those skilled in the art upon a reading of the Detailed Description of the invention set forth below taken together with the drawings which will be described in the next section.

BRIEF DESCRIPTION OF THE DRAWINGS

The invention may take physical form in certain parts and arrangement of parts, a preferred embodiment of which will be described in detail and illustrated in the accompanying drawings which forms a part hereof and wherein.

DESCRIPTION OF PREFERRED EMBODIMENTS

Figure 1:
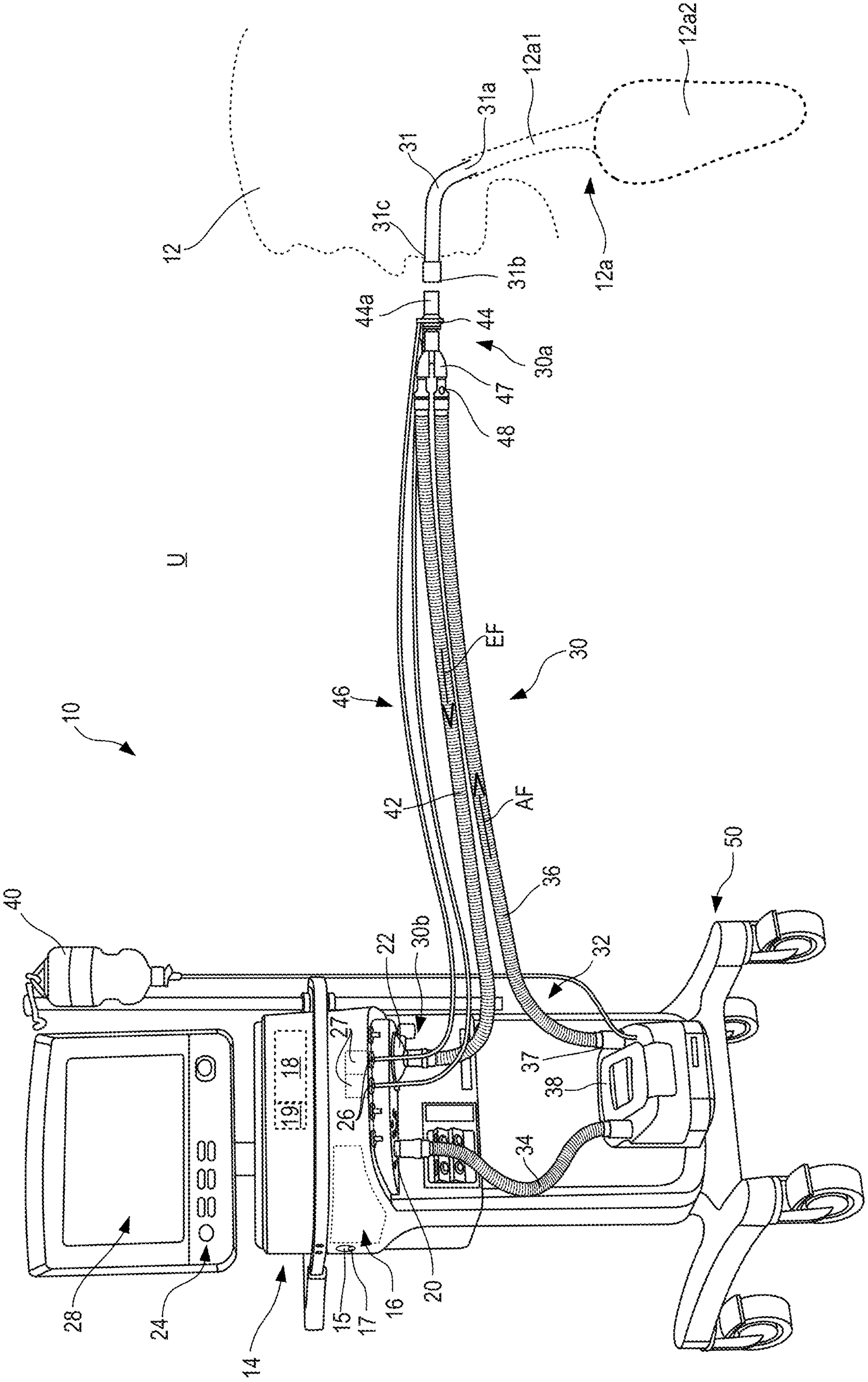
FIG. 1A schematic depiction of a ventilation apparatus according to the invention arranged for artificial ventilation of a patient, and FIG. 2A graphic output of a temporal course of the respiratory tract content of respiratory gas of an artificially ventilated patient, produced once each with a conventional determination method and with the method proposed here, and FIG. 3A flowchart of a sequence of an embodiment according to the invention of the method proposed here.

Referring now to the drawings wherein the showings are for the purpose of illustrating preferred and alternative embodiments of the invention only and not for the purpose of limiting the same, in FIG. 1, an embodiment according to the invention of a ventilation apparatus is labelled generally by 10. The ventilation apparatus 10 serves in the depicted example for artificial ventilation of a-preferably human-patient 12.

The ventilation apparatus 10 exhibits a housing 14 in which an aspiration port 15 is configured and—not discernible from outside because of the opaque housing material—a flow modification device 16 and a control device 18 are accommodated. The aspiration port 15 allows the flow modification device 16 to aspirate ambient air from the external environment U of the ventilation apparatus and after cleaning which is known per se by filters to supply it as respiratory gas to the patient 12. The aspiration port 15 is therefore a respiratory gas source arrangement in terms of the present application.

In the aspiration port 15 there can be situated an ambient temperature sensor 17 which measures the temperature of the air of the environment U and transmits it to the control device 18.

The flow modification device 16 is constructed in a manner which is known per se and can exhibit a pump and/or a compressor and/or a fan and/or a pressure container and/or a reducing valve and the like. The ventilation apparatus 10 further exhibits in a manner which is known per se an inspiration valve 20 and an expiration valve 22.

The control device 18 is usually realized as a computer or microprocessor. It comprises a data store labelled by 19 in FIG. 1, in order to be able to store and where required retrieve data necessary for the operation of the ventilation apparatus 10. In the case of network operation, the data store

19 can also be located outside the housing 14 and be linked via a data transmission link with the control device 18. The data transmission link can be formed by a cable path or a radio path. However, in order to prevent interference in the data transmission link being able to impact the operation of the ventilation apparatus 10, the data store 19 is preferably integrated in the control device 18 or at least is accommodated in the same housing 14 as it.

For the input of data into the ventilation apparatus 10 or more precisely into the control device 18 as the case may be, the ventilation apparatus 10 can exhibit an input device 24 which in the example depicted in FIG. 1 is represented by a keyboard. As will be further elucidated below, the keyboard is not necessarily the only data input of the control device 18. In fact, the control device 18 can additionally or alternatively to the keyboard receive data via various data inputs, for instance via a network cable, a radio path, or via sensor connectors 26.

For the output of data to the treating therapist, the ventilation apparatus 10 can exhibit an output device 28 exhibit, in the depicted example a monitor.

For artificial ventilation, the patient 12 is connected with the ventilation apparatus 10, more accurately with the flow modification device 16 in the housing 14, via a respiratory gas line arrangement 30. To this end, the patient 12 is intubated by means of an endotracheal tube as a patient interface 31. A proximal longitudinal end 31*a* of the patient interface 31 delivers the inspiratory respiratory gas flow AF into the respiratory tract 12*a* of the patient 12. Through the proximal longitudinal end 31*a* there also flows the expiratory respiratory gas flow EF into the respiratory gas line arrangement 30.

The respiratory tract 12*a* of patient 12 comprises the latter's upper airways 12*a*1 and the latter's lower airways 12*a*2. The body organ commonly referred to as 'lung' belongs to the lower airways 12*a*2.

A distal longitudinal end 31*b* of the patient interface 31 is configured for connecting with the respiratory gas line arrangement 30. From the location 31*c* in the inspiration direction downstream to the proximal longitudinal end 31*a*, the patient interface is surrounded by the body of the patient 12. This means conversely that from its distal longitudinal end 31*b* up to the location 31*c*, the patient interface 31 is exposed to the external environment U and is in heat transfer, predominantly convective, contact with it.

The respiratory gas line arrangement 30 exhibits an inspiration hose 32, over which fresh respiratory gas can be conveyed from the flow modification device 16 into the respiratory tract 12*a* of the patient 12. The inspiration hose 32 can be discontinuous and exhibit a first inspiration hose 34 and a second inspiration hose 36, between which a humidification device 38 can be provided for targeted humidification and where appropriate also temperature control of the inspiratory respiratory gas supplied to the patient 12. The humidification device 38 can be connected with an external fluid reservoir 40, via which water for humidification or also a medication, e.g. for anti-inflammatory purposes or for airway dilatation, can be added to the humidification device 38. When deploying the present ventilation apparatus 10 as an anesthesia ventilation apparatus, in this way volatile anesthetics can be administered to the patient 12 in a controlled manner via the ventilation apparatus 10. The humidification device 38 makes sure that the fresh respiratory gas is supplied to the patient 12 at a predetermined humidity, where appropriate with the addition of a medication aerosol, and at a predetermined temperature.

The second inspiration hose 36 is heatable electrically in the present example through a line heating device 37. The line heating device 37 can be actuated for operation by the control device 18. The above notwithstanding, the first inspiration hose 34 can also be heatable and/or the at least one hose 34 and/or 36 can be heatable through other than an electrical line heating device 37, for instance by flushing around with a heat-exchange medium.

The respiratory gas line arrangement 30 further exhibits, besides the already mentioned inspiration valve 20 and expiration valve 22, an expiration hose 42 via which metabolized respiratory gas is discharged as expiratory respiratory gas flow EF from the respiratory tract 12*a* of the patient 12 into the external environment U.

At the distal longitudinal end 30*b* of the respiratory gas line arrangement 30, there are coupled the inspiration hose 32 with the inspiration valve 20 and the expiration hose 42 with the expiration valve 22. Of the two valves, preferably only one at a time is opened concurrently to let a gas flow through. The actuation control of valves 20 and 22 takes place likewise through the control device 18.

During a ventilation cycle, initially the expiration valve 22 is closed for the duration of the inspiration phase and the inspiration valve 20 opened, such that fresh inspiratory respiratory gas can be conducted from the housing 14 to the patient 12. A flow of the fresh respiratory gas is effected through a targeted pressure increase of the respiratory gas through the flow modification device 16. Due to the pressure increase, the fresh respiratory gas flows into the respiratory tract 12*a* of the patient 12 and there expands the body region near to the respiratory tract, i.e. in particular the thorax, against the individual elasticity of the body parts near to the respiratory tract. The gas pressure inside the respiratory tract 12*a* of the patient 12 also rises thereby.

At the end of the inspiration phase, the inspiration valve 20 is closed and the expiration valve 22 opened. The expiration phase begins. Due to the gas pressure of the respiratory gas present in the respiratory tract 12*a* of the patient 12 which is elevated until the end of the inspiration phase, after opening of the expiration valve 22 it flows into the external environment U, whereby the gas pressure in the respiratory tract 12*a* of the patient 12 decreases with progressing flow duration. Once the gas pressure in the respiratory tract 12*a* reaches a positive end-expiratory pressure (PEEP) set in the ventilation apparatus 10, that is, a slightly higher pressure than the atmospheric pressure, the expiration phase ends with the closing of the expiration valve 22 and there follows a further ventilation cycle.

During the inspiration phase, there is supplied to the patient 12 for example in a volume-relatedly controlled supporting ventilation mode the ventilation tidal volume, i.e. the respiratory gas volume per breath, set for the patient 12. The ventilation tidal volume multiplied by the number of ventilation cycles per minute, that is, multiplied by the ventilation frequency, yields the volume per minute of the artificial ventilation performed in the present case.

The ventilation apparatus 10, in particular the control device 18, is preferably configured to repeatedly update and/or ascertain respectively during the ventilation operation ventilation operational parameters which distinguish the ventilation operation of the ventilation apparatus 10, in order to make sure that at each point in time the ventilation operation is matched as optimally as possible to the respective patient 12 to be ventilated. Especially advantageously, the determination of one or several ventilation operational parameters takes place at the ventilation frequency, such that for each ventilation cycle current and thereby optimally adjusted to the patient 12 ventilation operational parameters can be provided.

To this end, the ventilation apparatus 10 can be linked for data transmission with one or several sensors which monitor the condition of the patient and/or the operation of the ventilation apparatus 10. The ventilation apparatus 10 exhibits as such a sensor a proximal differential pressure flow sensor 44, which acquires quantitatively the respiratory gas flow prevailing in the respiratory gas line arrangement 30, namely both the inspiratory respiratory gas flow AF and the expiratory respiratory gas flow EF. The proximal differential pressure flow sensor 44 is coupled by means of a sensor line arrangement 46 with the data inputs 26 of the control device 18. The sensor line arrangement 46 can, but does not have to, comprise electrical signal transmission lines. It can likewise exhibit hose lines which transmit the gas pressure prevailing in the flow direction on both sides of a flow resistance of the differential pressure flow sensor 44 to the data inputs 26, where these are quantified by pressure sensors 27.

More precisely, the respiratory gas line arrangement 30 exhibits in the preferred embodiment example at its proximal longitudinal end region 30*a* a separately configured Y-line section 47, which at its distal end region is connected with the second inspiration hose 36 and with the expiration hose 42 and which at its proximal end region is connected with the proximal flow sensor 44.

The proximal flow sensor 44 exhibits at its proximal end region a coupling formation 44*a*, with which the patient interface 31, which instead of a tube can also be a mask, is couplable with the proximal flow sensor 44 and thus with the respiratory gas line arrangement 30.

The second inspiration hose 36 can exhibit at its proximal longitudinal end region a proximal temperature sensor 48, which measures the temperature of the respiratory gas flow AF in the second inspiration hose 36 as closely as possible to the patient 12 and transmits it to the control device 18.

Solely for the sake of completeness it is pointed out that the ventilation apparatus 10 according to the invention can be accommodated on a rollable rack 50 as a mobile ventilation apparatus 10.

Figure 2:
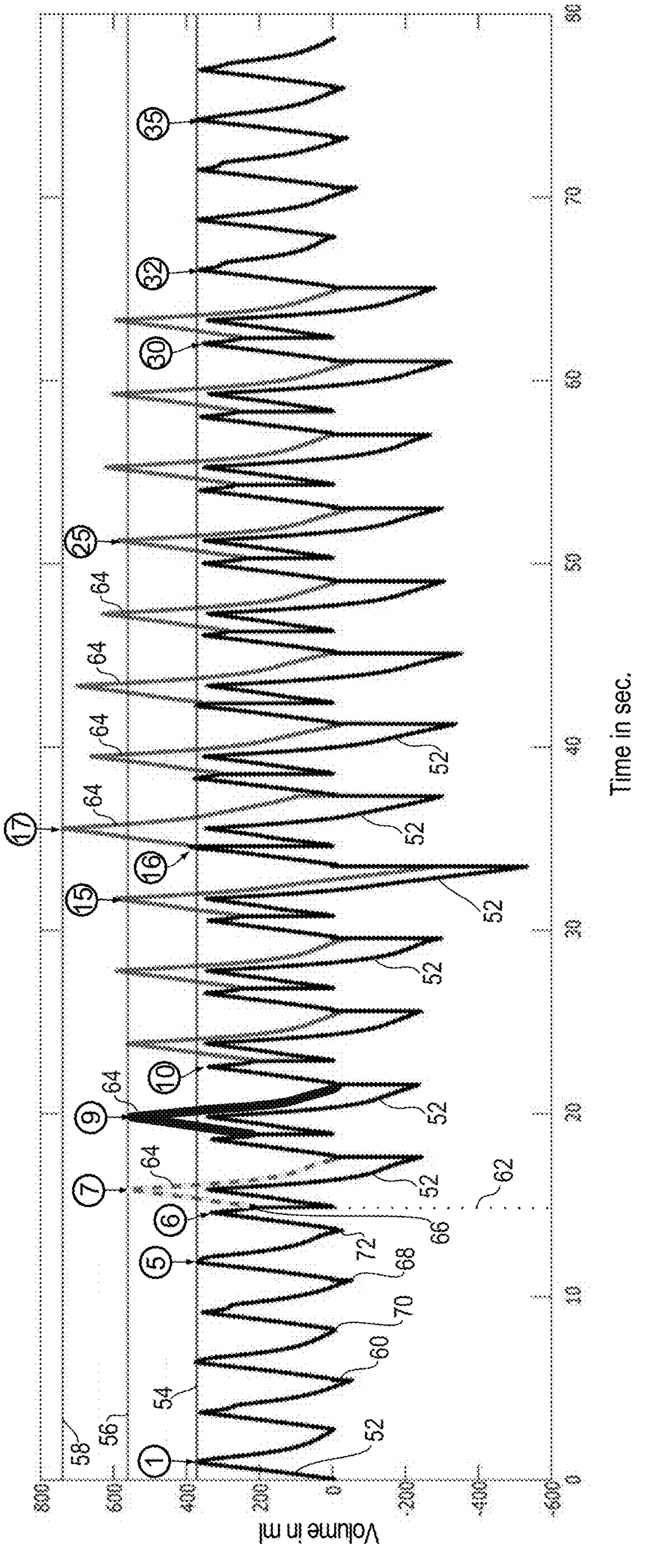

In FIG. 2 there is shown by way of example a graphic output of the respiratory gas quantity balance of the patient 12 over several breaths. The abscissa of the coordinate system of FIG. 2 indicates the time in seconds, the ordinate the respiratory gas quantity currently remaining in the patient 12, i.e. the respiratory tract content of respiratory gas, as respiratory gas volume in milliliters.

A graph 52 shows as a respiratory gas quantity balance the result of a conventional method for determining a respiratory gas quantity currently remaining in the patient 12 as respiratory tract content of respiratory gas. In the conventional determination of the respiratory tract content of respiratory gas of patient 12, the initial quantity value of the respiratory gas quantity balance is reset to zero by the control device 18 before each breath in order to prevent drift of the signal 52. Such drift could be effected through faulty calibration and/or through manufacturing tolerances of the differential pressure flow sensor 44. The manufacturing tolerances can have an impact to the effect that for quantitatively one and the same respiratory gas flow, the differential pressure flow sensor 44 outputs and/or generates as the case may be inspiratory and expiratory flow signals that differ quantitatively slightly from one another.

The control device 18 integrates over the duration of one breath, for determining the respiratory tract content of respiratory gas, the flows acquired by the differential pressure flow sensor 44. In the depiction of FIG. 2, each local upper peak of graph 52 corresponds to a different breath, where the rising flank is created by the inspiration process of a breath and the falling flank by the expiration process of the same breath. Since in conventional determination, the respiratory gas quantity balance and/or the respiratory tract content of respiratory gas respectively begins at zero at the beginning of each breath, inspiratory respiratory gas flows are integrated with positive magnitudes and expiratory respiratory gas flows with negative magnitudes. The breaths are denoted below by consecutive numbers, beginning with breath No. 1 at 0 seconds. To facilitate orientation, several breaths are identified by their numbers in a circle.

Line 54 indicates a target respiratory gas quantity and/or a target respiratory tract content of respiratory gas respectively at the end of an inspiration phase of each breath. This target respiratory tract content of respiratory gas corresponds to the aforementioned ventilation tidal volume.

Line 56, which is parallel to line 54, indicates a first limit of a respiratory tract content of respiratory gas which corresponds to 1.5 times the target value of the ventilation tidal volume. Line 58 indicates a second limit of the respiratory tract content of respiratory gas, which corresponds to twice the target value of the ventilation tidal volume.

The respiratory gas quantity balance depicted in FIG. 2 is a theoretically generated respiratory gas quantity balance, in order to visualize the method being applied here. It is not a respiratory gas quantity balance ascertained in a real patient.

In breaths No. 2 and No. 4 of FIG. 2 there occurs excessive expiration, in which the patient 12 exhales more respiratory gas than administered to them previously during the inspiration phase. This can arise, for example, through mild coughing at the end of the expiration or through a spontaneous cessation of a flow obstruction, for instance of a mucus accumulation in the airways. It is clearly discernible how the subsequent breath No. 3, in relation to the earlier breath No. 2 at the beginning of the determination of the respiratory tract content of respiratory gas, is compulsorily set to zero by the control device during the subsequent breath No. 3, which is discernible at the vertical line section 60 connecting the end of the expiration of breath No. 2 with the beginning of the inspiration of breath No. 3. The same applies to the subsequent breath No. 5 in relation to its directly preceding earlier breath No. 4.

The depicted excessive expiration, at which the graphically depicted respiratory gas quantity balance becomes negative, can for example happen thereby that for each breath the integration of the respiratory gas flows occurring over the course of its duration begins at zero and is not integrated beyond the end of a breath. Not to be forgotten here, however, is the fact that breath No. 1 does indeed begin at a respiratory gas quantity of zero, but in the respiratory tract 12*a* of the patient 12 at this point in time there was present a positive respiratory gas quantity different from zero as an initial respiratory tract content of respiratory gas.

The ventilation apparatus 10 works in the depicted example in a volume-relatedly controlled support ventilation mode, according to which the set ventilation tidal volume is administered to the patient 12 either when in the respiratory gas line the PEEP is acquired which indicates the end of an inspiration, or when the patient 12 exhibits spontaneous breathing, that is, exerts an inspiration effort and/or triggers an inspiration respectively.

As is clearly discernible in FIG. 2, the expiration process is incomplete in breath No. 6 and ends through triggering of an inspiration process at approximately 15 seconds (dotted line 62). Due to the signal drift-preventing convention of the conventional method for determining the respiratory tract content of respiratory gas of patient 12, for the subsequent breath No. 7 which follows the earlier breath No. 6 the starting value of the respiratory tract content of respiratory gas and/or of the respiratory gas quantity balance respectively is set to zero, from where the inspiration process of breath No. 7 is plotted by graph 52.

Due to the permanent resetting of the respiratory tract content of respiratory gas of the patient 12 at the beginning of a breath, breath No. 7 also appears in graph 52 as though only the ventilation tidal volume is properly supplied to the patient 12. As a consequence of the respiratory tract 12*a* being in fact overfilled with respiratory gas during breath No. 7, when using the conventional method there occurs in graph 52 at the end of breath No. 7 a drastic apparent over-emptying of the respiratory tract 12*a* of the patient.

In fact, the over-emptying depicted in graph 52 at the end of breath No. 7 does not take place. The passive expiration, which normally is only driven by the overpressure generated in the respiratory tract of the patient 12*a* during inspiration relative to the ambient atmosphere as the sink for expiratory respiratory gas, effects merely a discharge of the respiratory tract content of respiratory gas, which is overlarge due to the preceding incomplete expiration in breath No. 6, after the end of the inspiration process of breath No. 7.

Graph 64 in FIG. 2 shows the respiratory tract content of respiratory gas determined in accordance with the method according to the invention being described here. This proceeds in the control device 18 according to the flowchart depicted in FIG. 3.

The control device 18 interrogates at a frequency f the respiratory gas flow values acquired by the differential pressure flow sensor 44. Consequently, the control device 18 receives a new respiratory gas flow value on each expiration of a time $\Delta t=1/f$.

Figure 3:
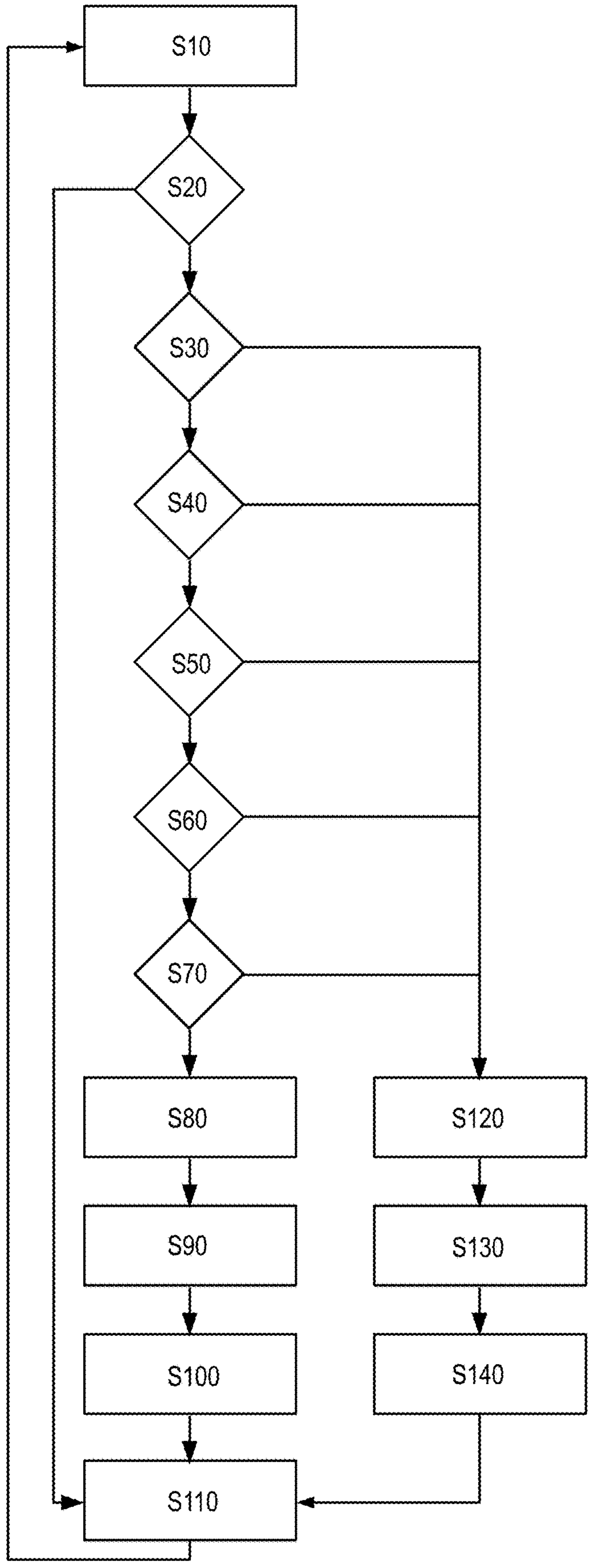

In step S10 in FIG. 3, the control device 18 interrogates the differential pressure flow sensor 44 and receives as answer a respiratory gas flow value F.

In the following step S20, the control device 18 checks whether the respiratory gas flow value F was acquired at the beginning of a new breath, i.e. at the beginning of a new inspiration phase, since only at the beginning of a new breath is it to be checked at all whether the respiratory tract content of respiratory gas of an earlier breath ascertained thus far should be updated through appropriate setting of a starting value for determining the respiratory tract content of respiratory gas for the newly beginning subsequent breath or whether the determination of the respiratory tract content of respiratory gas should begin at zero.

When the obtained respiratory gas flow value F was acquired at the beginning of a subsequent breath, the method proceeds to step S30 in which a decision value is ascertained and compared with a decision threshold value.

The decision value is, for example, the difference value of the earlier breath based on the inspiratory respiratory gas quantity of the preceding earlier breath, which quantifies a balance difference between inspiratory and expiratory respiratory gas quantity of the earlier breath.

Since the earlier breath No. 6 began with a starting value of 0 ml, at point 66 in FIG. 2, at which the expiration in the earlier breath No. 6 ends prematurely and the subsequent breath No. 7 begins, the value of the respiratory gas quantity balance according to graph 52 (and also according to graph 64, which at this point is still congruent with graph 52) is the difference value between the respiratory gas quantity inhaled in the earlier breath No. 7 and the respiratory gas quantity exhaled in the same breath No. 7. The difference value equals approximately 220 ml. The inspiratory respiratory gas quantity of the earlier breath No. 6 is the local peak value of graph 52, at which the gradient of graph 52 reverses. It equals approximately 340 ml.

The decision value therefore equals 220 ml/340 ml=0.65. Based on previous experiments and investigations, a value of 0.25 was chosen as decision threshold value. The decision value exceeds the decision threshold value, such that the method proceeds to step S40.

In step S40 it is examined whether an incremental counting variable, with which the frequency of a directly consecutive occurrence of exceedances of the decision threshold value by the decision value is counted, is smaller than or equal to a predetermined limit which indicates a maximum permissible number of directly consecutive exceedances of the decision threshold value. In the present case, the predetermined limit equals 3.

Since in the earlier breaths Nos. 1 to 6 thus far the decision threshold value was not exceeded because of the essentially complete expiration, but rather this happens for the first time at the beginning of the subsequent breath No. 7, the method proceeds to step S50.

In step S50 it is examined whether Equation 1 stated above was not satisfied at a frequency above 50% for the last 10 breaths, where on the basis of experiments and medical investigations 0.2 is chosen for the ratio threshold value.

Since no preceding 10 breaths existed until the beginning of the subsequent breath No. 7, step S50 is performed for the existing number of preceding 6 breaths.

The application of Equation 1 is elucidated below using the example of breath No. 4, with i=4: The end-expiratory respiratory gas volume of breath No. 4, see point 68, equals approximately-30 ml. The end-expiratory respiratory gas volume of the preceding breath No. i−1=3, see point 70, equals approximately 0 ml. The end-inspiratory respiratory gas volume of breath No. 4 lies just below the target ventilation tidal volume at approximately 350 ml. Equation 1 yields from these values for the left side of Equation 1 the value −0.08, which if only because of the negative sign is certainly no greater than the ratio threshold value of 0.2. The result looks similar for the remaining breaths of Nos. 1 to 6, the ratio threshold value was not exceeded. Consequently, Equation 1 was satisfied in the breaths preceding the subsequent breath No. 7 for fewer than half of the breaths, whereby the frequency threshold value, which by way of example equals a value of 50%, was not reached. The method then proceeds to step S60.

In step S60 it is checked whether in the earlier breath No. 5 there took place an excessively large expiration relative to the directly preceding breath No. 6. A large expiration, in which more respiratory gas is exhaled by the patient 12 than was previously inhaled, results in a negative end-expiratory respiratory gas volume. The criterion for there being no excessively large expiration is whether the end-expiratory respiratory gas volume of the directly preceding earlier breath No. 6 is greater than the negative end-expiratory respiratory gas volume of the earlier breath No. 5 (s. Equation 2).

$$V_{endexp,i} > -V_{endexp,i-1} \qquad \text{Eq. 2}$$

The end-expiratory respiratory gas volume of breath No. 5 is indeed negative, but at approximately −25 ml only slightly so. The end-expiratory respiratory gas volume of breath No. 6 at approximately 220 ml is greater than the end-expiratory respiratory gas volume of breath No. 5 multiplied by −1. Therefore the method proceeds to step S70.

In step S70 it is examined whether in a predetermined time interval before the subsequent breath No. 7, for instance during the preceding last two breaths No. 5 and No. 6, the PEEP was increased, which is not the case. Consequently, the method proceeds to step S80.

Once step S80 has been reached, it is clear that all the criteria for recognizing incomplete expiration and thus breath stacking have been met. In step S80, the ventilation mode is changed from the volume-relatedly controlled supported ventilation performed thus far to pressure-relatedly controlled supported ventilation. Furthermore, as a pressure support value for the changed ventilation mode, preferably a pressure value is set which is adjusted to the mean end-inspiratory respiratory gas pressure of a predetermined number of directly preceding breaths, for instance the last 10 breaths, less the PEEP. The renewed administration of the tidal volume should hereby be prevented after a recognized incomplete expiration. The method then proceeds to step S90.

Step S80 of a change to the ventilation mode is only one possible variant of the method. Often, the autonomous changing of the ventilation mode by the ventilation apparatus is not desired by treating therapists. The method can also proceed directly from step S70 to step S90.

In the ventilation process depicted graphically in FIG. 2, no change in the ventilation mode has taken place.

In step S90, the counting variable which indicates the frequency of incomplete expiration occurring directly in succession is increased by 1. The method then proceeds to step S100.

In step S100, the end-expiratory respiratory gas volume of the directly preceding earlier breath No. 6 is set as continuity starting value for determining the respiratory tract content of respiratory gas during the subsequent breath No. 7. The method then proceeds to step S110.

In step S110, the respiratory gas volume that has flowed thus far is ascertained through numerical integration from the respiratory gas flow obtained in step S10. It is assumed here that until the acquisition of the next respiratory gas flow, i.e. for the duration Δt, there flows the acquired respiratory gas flow F. The respiratory tract content of respiratory gas AL ascertained in step S110 for the kth acquired respiratory gas flow out of a total of n respiratory gas flows of the considered subsequent breath thus corresponds to the following Equation 3:

$$AL(k) = V_{Starting\ value} + \sum_{k=1}^{n} F(k) \cdot \Delta t \qquad \text{Eq. 3}$$

where $V_{Starting\ value}$ is the starting value for determining the respiratory tract content of respiratory gas in the subsequent breath. As described above, after traversing the method branch containing step S100 the starting value is the continuity starting value, i.e. the end-expiratory respiratory gas volume in the respiratory tract of the patient in the earlier breath directly preceding the subsequent breath.

After performing the numerical integration in step S110, the method returns to step S10 where the next respiratory gas flow is acquired.

Since the method serves only to determine a starting value for a determination of a respiratory tract content of respiratory gas of the patient 12, the method proceeds at step S20 accordingly if the acquired respiratory gas flow does not stand at the start of a breath, directly to the numerical integration of step S110.

Steps S40 to S70 do not have to be performed, but increase the accuracy of the method. The method can also solely in step S30 based on the formation of the decision value and its comparison with a decision threshold value lead to the process branches with steps S100 or S140.

When in one of the steps S30 to S70 one of the mentioned criteria is not assessed as described above, the method sequence does not reach steps S80 or S90 but rather ends up in the alternative branch, where step S120 is processed next.

Step S120, which does not necessarily have to be present, confirms the continuation of the volume-relatedly controlled, supporting ventilation mode chosen thus far.

In any case, under differing criteria assessment in one of the steps S30 to S70 there is reached the alternative step S130 corresponding to the previously elucidated step S90, in which the counting variable for counting the frequency of directly consecutive breath stackings, i.e. incomplete expiration, is reset to zero, since the directly preceding earlier breath did not exhibit breath stacking.

The method then proceeds to step S140, in which the starting value for determining the respiratory tract content of respiratory gas for the subsequent breath is reset to the reset starting value zero. This means that when the method branch with step S140 is traversed, $V_{Starting\ value}$ equals zero.

Afterwards the method proceeds to step S110 already elucidated above, in which the numerical integration of the acquired type flow F(k) takes place.

For better clarity, in FIG. 2 the graph 52, which conventionally shows the respiratory tract content of respiratory gas of the patient 12 with the resetting of the starting value to zero before each breath, and the graph 64, which shows the ascertaining of the respiratory tract content of respiratory gas of the patient 12 in accordance with the method presented here, are provided several times with reference labels. In principle it is the case that in FIG. 2 the graph sections that are well below the zero line belong to graph 52 and the peak values that approximately or completely reach line 56 belong to graph 64. Between graph 64 merging with graph 52 and renewed separation of graph 64 from graph 52, the two graphs 64 and 52 proceed along a common line, which is explained by the common integration rule.

In order to make the incomplete expiration and the subsequent renewed administration of the tidal volume as easily, rapidly, and reliably recognizable as possible for a therapist who is viewing the graphic output of the respiratory tract content of respiratory gas, the control device 18 is configured to change the graphic depiction of the respiratory tract content of respiratory gas as a function of time from the point in time at which the continuity starting value is set as the respiratory tract content starting value. This change in the depiction can, for example, continue until reaching an end-expiratory respiratory tract content which falls below a predetermined graphic changing threshold value or no longer differs quantitatively as a predetermined graphic changing value from the mean end-expiratory respiratory tract content of the last n breaths, where for example n can be 5 or 10 or another whole number.

For breath No. 7, by way of example, the graphic output of the respiratory tract content of respiratory gas is changed by changing the line type and the line color. For breath No. 9, by way of example, the graphic output of the respiratory tract content of respiratory gas is changed by changing the line weight from thinner to thicker.

In breath No. 7, after the incomplete expiration of breath No. 6, the results of the conventional determination of the respiratory tract content of respiratory gas and the results of the determination according to the method being discussed here differ for the first time. There follows then breath No. 8 with again incomplete expiration, a normal breath No. 9, breath No. 10 with incomplete expiration, whereupon there always follow breaths with an even number until breath No. 30, which exhibit incomplete expiration, after which there follow breaths with odd numbers and complete expiration. From breath No. 32, including this breath, no more breath stackings occur.

The following characteristic features should be pointed out: At the end of the expiration of breath 15, the patient 12 breathes deeply out such that the end-expiratory respiratory gas quantity in the respiratory tract of the patient 12*a* becomes negative. Since the end-inspiratory respiratory gas quantity of breath 15 is positive, like every end-inspiratory respiratory gas quantity besides, the decision value ascertained in step S30 is likewise negative and thus smaller than the decision threshold value. As a consequence, the reset starting value is set as the respiratory tract content starting value for determining the respiratory tract content of respiratory gas of the subsequent breath No. 16.

In breath No. 16, the patient 12 triggers a further inspiration phase directly after the end of the inspiration, such that a second tidal volume is administered to the patient 12 directly subsequent to a first tidal volume. After the subsequent expiration in breath No. 17, because of the high end-inspiratory respiratory gas quantity of breath No. 17 the decision value formed in step S30 is lower than the decision threshold value, such that for the following subsequent breath No. 18 the reset starting value is set as the respiratory tract content starting value.

The graphic depiction of the ventilation process by displaying the respiratory tract content of respiratory gas as a function of time in FIG. 2 with graph 64, avoids undesirable drift and nonetheless provides intuitively better comprehensible information about the inspiratory and expiratory respiratory gas volumes of the ventilation process.

While considerable emphasis has been placed on the preferred embodiments of the invention illustrated and described herein, it will be appreciated that other embodiments, and equivalences thereof, can be made and that many changes can be made in the preferred embodiments without departing from the principles of the invention. Furthermore, the embodiments described above can be combined to form yet other embodiments of the invention of this application. Accordingly, it is to be distinctly understood that the foregoing descriptive matter is to be interpreted merely as illustrative of the invention and not as a limitation.

The invention claimed is:

1. A method for determining respiratory gas content in a respiratory tract, which is present in the respiratory tract of an at least partially artificially ventilated patient after several breaths performed under the participation of a ventilation apparatus, where the several breaths exhibit at least one earlier breath set and at least one subsequent breath following the earlier breath set, where the earlier breath set exhibits one earlier breath or a plurality of successive earlier breaths, where the method comprises quantitative acquisition of inspiratory and expiratory respiratory gas flows through at least one respiratory gas flow sensor and summation of acquired inspiratory and expiratory flow values to the respiratory tract content of respiratory gas, wherein a respiratory tract content starting value, with which the determination of the respiratory gas content in the respiratory tract for the at least one subsequent breath begins, depending on a respiratory gas quantity difference between an inspiratory respiratory gas quantity supplied to the at least partially artificially ventilated patient during the earlier breath set and an expiratory respiratory gas quantity exhaled by the at least partially artificially ventilated patient during the earlier breath set, is set to a reset starting value lying nearer to zero than to a difference value indicating quantitatively the respiratory gas quantity difference or to a continuity starting value lying nearer to the difference value than to zero.

2. The method according to claim 1, wherein the reset starting value is zero and/or the continuity starting value is the difference value.

3. The method according to claim 1, wherein the respiratory tract content starting value is determined repeatedly during the at least partial artificial ventilation of a patient.

4. The method according to claim 3, wherein the reset starting value is determined independently from the respiratory gas quantity difference as the respiratory tract content starting value when previously in a predetermined first number of successive determinations of the respiratory tract content starting value each time the continuity starting value was determined as the respiratory tract content starting value.

5. The method according to claim 3, wherein the reset starting value is determined independently from the respiratory gas quantity difference as the respiratory tract content starting value when previously within a predetermined second number of determinations of the respiratory tract content starting value the number of determinations which had as a result the continuity starting value reaches or exceeds a predetermined fraction threshold value, where the fraction threshold value is smaller than the second number.

6. The method according to claim 3, wherein the reset starting value is determined as the respiratory tract content starting value independently from the respiratory gas quantity difference when previously within a predetermined number of breaths it is the case that the frequency at which a ratio of a first respiratory tract content difference and a second respiratory tract content difference which differs from the first reaches or exceeds a predetermined ratio threshold value, reaches or exceeds a frequency threshold value, where preferably the first respiratory tract content difference is a difference between the respiratory gas content in the respiratory tract at the end of a particular breath and the respiratory gas content in the respiratory tract at the end of an earlier breath set preceding the particular breath and/or where the second respiratory tract content difference is a difference between a respiratory gas content in the respiratory tract at the end of an inspiration phase of the determined breath and the respiratory gas content in the respiratory tract at the end of the earlier breath set preceding the particular breath.

7. The method according to claim 1, wherein the method comprises ascertaining a decision value, where the decision value represents the respiratory gas quantity difference, in particular the difference value, where depending on the decision value the reset starting value or the continuity starting value is determined as the respiratory tract content starting value for the at least one subsequent breath.

8. The method according to claim 7, wherein the decision value is proportional to a ratio of the difference value and an inspiratory respiratory gas quantity supplied to the at least partially artificially ventilated patient under the participation of the ventilation apparatus during the earlier breath set.

9. The method according to claim 7, wherein the determination of the respiratory tract content starting values comprises, in dependence on the decision value, a comparison of the decision value with a predetermined decision threshold value, where the respiratory tract content starting value is determined in dependence of a result of the comparison.

10. The method according to claim 1, wherein the reset starting value is determined as the respiratory tract content starting value independently from the respiratory gas quantity difference when for at least one of the two earlier breath sets directly preceding the current subsequent breath for which the respiratory tract content starting value is being determined, it is ascertained that an expiratory respiratory gas volume of the earlier breath set ascertained from the acquired expiratory respiratory gas flows is quantitatively greater than an inspiratory respiratory gas volume of the same earlier breath set ascertained from the inspiratory respiratory gas flows.

11. The method according to claim 1, wherein the reset starting value is determined as the respiratory tract content starting value independently from the respiratory gas quantity difference when within a predetermined time interval before the current determination of the respiratory tract content starting value a quantitative change in the PEEP was acquired.

12. The method according to claim 1, wherein the respiratory gas content in the respiratory tract is output graphically as a function of time at an output device.

13. The method according to claim 12, wherein when the continuity starting value is set as the respiratory tract content starting value, the graphic output of the respiratory tract content is changed as a function of time.

14. A ventilation apparatus for at least partial artificial ventilation of the at least partially artificially ventilated patient, comprising:

a respiratory gas source arrangement which provides an inspiratory respiratory gas for artificial ventilation of the at least partially artificially ventilated patient, a flow modification device which is configured create and quantitatively to modify an inspiratory respiratory gas flow, a respiratory gas line arrangement with a proximal longitudinal end which during operation lies nearer to the at least partially artificially ventilated patient and with a distal longitudinal end which during operation lies further away from the at least partially artificially ventilated patient, in order to convey the inspiratory respiratory gas flow from the respiratory gas source arrangement up to the at least partially artificially ventilated patient, a flow sensor arrangement which is configured quantitatively to acquire the inspiratory respiratory gas flow and likewise an expiratory respiratory gas flow, a control device with a data store, where the control device is linked for signal transmission with the data store and with the flow sensor arrangement and which is configured to control the operational performance of the flow modification device for modifying the inspiratory respiratory gas flow, wherein the control device being configured to implement the method according to claim 1.

15. The ventilation apparatus according to claim 14, wherein the ventilation apparatus exhibits a graphic output device, and the control device wherein the respiratory gas content in a respiratory tract is outputted graphically as a function of time at an output device and/or wherein when the continuity starting value is set as the respiratory tract content starting value, the graphic output of the respiratory tract content is changed as a function of time.

16. The ventilation apparatus according to claim 14, wherein the ventilation apparatus is configured to perform artificial ventilation in a support ventilation mode, in which the control device acquires an inspiration effort of the ventilated patient and on acquiring the inspiration effort actuates the flow modification device to administer to the patient an inspiratory respiratory gas quantity via the respiratory gas line arrangement.

17. The ventilation apparatus according to claim 16, wherein the control device is configured to recognize an incomplete expiration on the basis of the determined respiratory tract content starting value and/or on the basis of the determined respiratory tract content of respiratory gas, and when the control device has recognized an incomplete expiration, to change the ventilation mode, in particular to change between a volume-relatedly controlled ventilation mode and a pressure-relatedly controlled ventilation mode.

18. The ventilation apparatus according to claim 14, wherein the flow sensor arrangement is a proximal flow sensor arrangement.

* * * * *